(12) United States Patent
Gmitro et al.

(10) Patent No.: US 10,754,144 B2
(45) Date of Patent: Aug. 25, 2020

(54) DITHERED FIBER-BUNDLE IMAGER AND HIGH-RESOLUTION IMAGING METHOD

(71) Applicant: Arizona Board of Regents on Behalf of the University of Arizona, Tucson, AZ (US)

(72) Inventors: Arthur Gmitro, Tucson, AZ (US); Andrew Rouse, Tucson, AZ (US); Neil Momsen, Tucson, AZ (US)

(73) Assignee: Arizona Board of Regents on Behalf of the University of Arizona, Tucson, AZ (US)

( * ) Notice: Subject to any disclaimer, the term of this patent is extended or adjusted under 35 U.S.C. 154(b) by 0 days.

(21) Appl. No.: 16/333,087

(22) PCT Filed: Sep. 22, 2017

(86) PCT No.: PCT/US2017/053027
§ 371 (c)(1),
(2) Date: Mar. 13, 2019

(87) PCT Pub. No.: WO2018/057935
PCT Pub. Date: Mar. 29, 2018

(65) Prior Publication Data
US 2019/0227299 A1 Jul. 25, 2019

Related U.S. Application Data

(60) Provisional application No. 62/398,410, filed on Sep. 22, 2016.

(51) Int. Cl.
*A61B 1/00* (2006.01)
*G02B 23/24* (2006.01)
(Continued)

(52) U.S. Cl.
CPC ...... *G02B 23/2484* (2013.01); *A61B 1/00167* (2013.01); *G02B 23/26* (2013.01);
(Continued)

(58) Field of Classification Search
CPC ........ A61B 1/0008; A61B 2017/00402; A61B 1/00167
See application file for complete search history.

(56) References Cited

U.S. PATENT DOCUMENTS 4,867,136 A * 9/1989 Suzuki ................. A61B 1/0008
600/109
8,347,409 B2 * 1/2013 Burns .................. G01Q 10/065
850/11
(Continued)

FOREIGN PATENT DOCUMENTS

WO WO 2015/098115 7/2015

OTHER PUBLICATIONS

International Search Report and Written Opinion of PCT/US2017/053027 dated Dec. 11, 2017, 7 pp.
(Continued)

*Primary Examiner* — Rowina J Cattungal
(74) *Attorney, Agent, or Firm* — Lathrop GPM LLP

(57) ABSTRACT

A method for high-resolution imaging includes: (i) forming, via a first lens, a first image at a first bundle-end of a fiber imaging bundle that has a second bundle-end opposite the first bundle-end and (ii) forming, via a second lens, an image of the second bundle-end onto an image sensor. The method also includes (iii) vibrating the first bundle-end relative to the first lens to dither the first image, and (iv) synchronously vibrating, relative to the vibrating first bundle-end, the second bundle-end relative to the second lens.

18 Claims, 8 Drawing Sheets

(51) Int. Cl.
*G02B 23/26* (2006.01)
*H04N 5/225* (2006.01)
*H04N 5/238* (2006.01)
*G02B 26/10* (2006.01)
*A61B 17/00* (2006.01)

(52) U.S. Cl.
CPC ......... *G02B 26/103* (2013.01); *H04N 5/2254* (2013.01); *H04N 5/238* (2013.01); *A61B 2017/00402* (2013.01); *H04N 2005/2255* (2013.01)

(56) References Cited

U.S. PATENT DOCUMENTS

| | | | | |
|---|---|---|---|---|
| 8,739,309 | B2* | 5/2014 | Hu | G01Q 60/30 850/5 |
| 9,274,139 | B2* | 3/2016 | Shi | B82Y 35/00 |
| 2008/0137363 | A1 | 6/2008 | Harris | |
| 2008/0249369 | A1* | 10/2008 | Seibel | G02B 23/26 600/182 |
| 2008/0277582 | A1* | 11/2008 | Shi | G01Q 10/04 250/309 |
| 2009/0032706 | A1* | 2/2009 | Prater | G01Q 20/02 250/307 |
| 2010/0157036 | A1* | 6/2010 | Sugimoto | G02B 23/2484 348/65 |
| 2015/0173606 | A1 | 6/2015 | Yu et al. | |
| 2016/0306164 | A1* | 10/2016 | Nishimura | A61B 1/00172 |
| 2017/0157831 | A1* | 6/2017 | Mandel | B29C 48/266 |

OTHER PUBLICATIONS

Engelbrecht et al. (2008) "Ultra-compact fiber-optic two-photon microscope for functional fluorescence imaging in vivo." Optics Express, vol. 16, No. 8, pp. 5556-5559.

\* cited by examiner

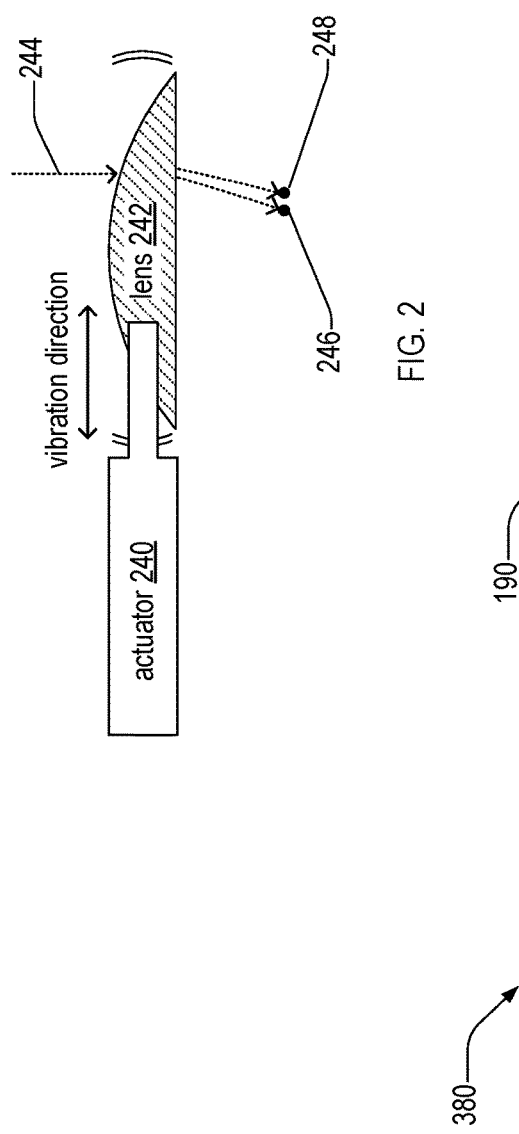
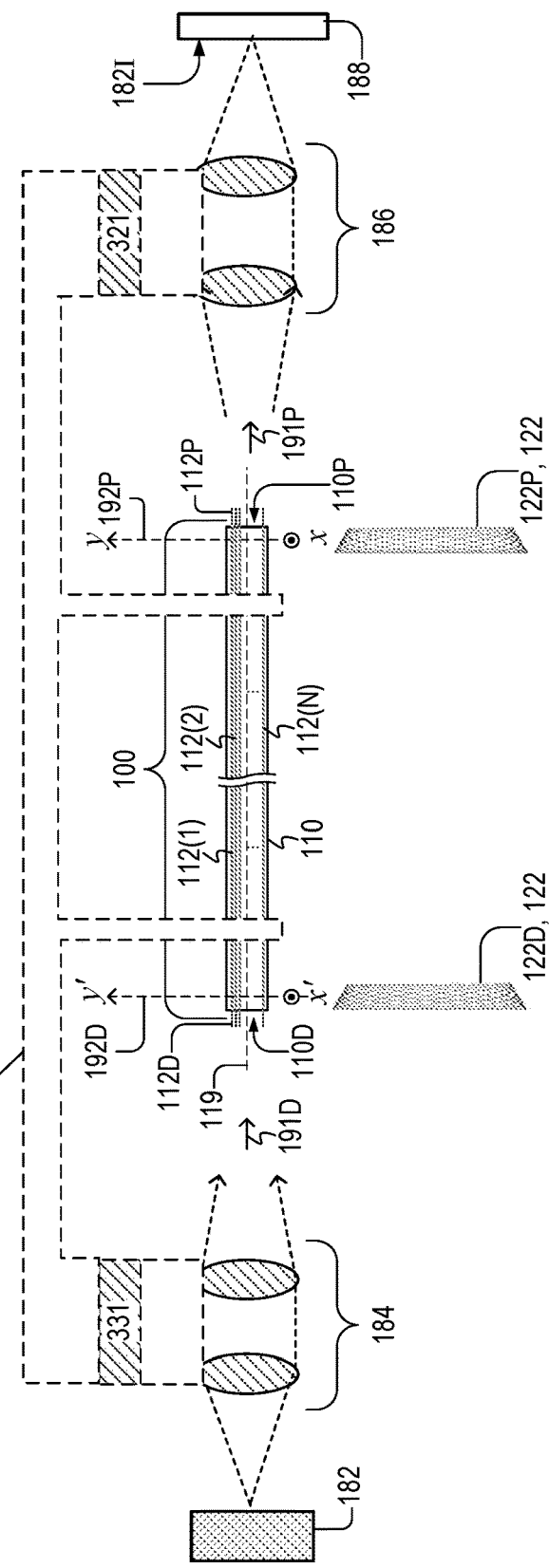

US 10,754,144 B2

DITHERED FIBER-BUNDLE IMAGER AND HIGH-RESOLUTION IMAGING METHOD

CLAIM TO PRIORITY

This application is a national phase entry under 35 U.S.C. § 371 of PCT/US2017/053027 filed on Sep. 22, 2017, which claims priority from U.S. Provisional Patent Application No. 62/398,410 filed Sep. 22, 2016, the contents of which are incorporated herein by reference.

U.S. GOVERNMENT RIGHTS

This invention was made with government support under Grant No. R01 CA115780 awarded by the National Institutes of Health. The government has certain rights in the invention.

BACKGROUND

Fiber bundle-based imaging systems employ a bundle of coherent imaging fibers to transfer an image from a distal end, where the object is located, to a proximal end, where the image is either recorded on a detector or viewed by an observer. The major advantage of fiber bundle imaging systems is their inherent flexibility and ability to reach remote areas, such as those inside the human body, which are difficult to reach with conventional imaging systems. However, the spatial resolution and space-bandwidth product and number of pixels in the images are limited by the physical structure of the fiber bundle. Because the fiber bundle only passes light incident on the fiber cores, light incident on the claddings is lost, which results in lowered throughput and a structured fixed pattern noise in the images. Moreover, the inherent sampling leads to potential aliasing of high spatial frequency information.

However, the spatial resolution and space-bandwidth product (# of pixels) in the images are limited by the physical structure of the fiber bundle. Because the fiber bundle passes only light incident on the cores, light incident on the cladding is lost, which results in lowered throughput and a structured fixed pattern noise in the images. Moreover, the inherent sampling, due to the non-zero core-to-core spacing of adjacent fibers in the fiber bundle leads to the potential for aliasing of high spatial frequency information.

SUMMARY

In a first embodiment, a dithered fiber-bundle imager is disclosed. The dithered fiber-bundle imager includes a fiber imaging bundle. The fiber imaging bundle includes (i) a plurality of optical fibers, (ii) a proximal bundle end exposing a respective proximal end of each of the plurality of optical fibers, and (iii) a distal bundle end exposing a respective distal end of each of the optical fibers. Each of the optical fibers have a respective optical axis parallel to (a) a proximal longitudinal direction at the proximal bundle end, and (b) a distal longitudinal direction at the distal bundle end. The imager also includes a first piezoelectric actuator configured to move a proximal device in a proximal plane orthogonal to the proximal longitudinal direction. The proximal device is one of (i) the proximal bundle end and (ii) a proximal lens. The imager also includes a second piezoelectric actuator configured to move a distal device in a distal plane orthogonal to the distal longitudinal direction, such that motion of the distal device and the proximal device are synchronized. The distal device is one of (i) the distal bundle end and (ii) a distal lens.

In a second embodiment, a method for high-resolution imaging is disclosed. The method includes: (i) forming, via a first lens, a first image at a first bundle-end of a fiber imaging bundle that has a second bundle-end opposite the first bundle-end and (ii) forming, via a second lens, an image of the second bundle-end onto an image sensor. The method also includes (iii) vibrating the first bundle-end relative to the first lens to dither the first image, and (iv) synchronously vibrating, relative to the vibrating first bundle-end, the second bundle-end relative to the second lens.

BRIEF DESCRIPTION OF THE FIGURES

FIG. 2 is a schematic view of how vibrating a lens off-center to a light path can shift or dither the resulting image.

FIG. 3 is a schematic view of an embodiment of a dithered fiber-bundle imager in an embodiment of an imaging system where the lenses are vibrated and fiber bundle stationary in a housing.

DETAILED DESCRIPTION OF THE EMBODIMENTS

To overcome the limitations discussed in the Background section, piezoelectric devices were employed to dither a fiber bundle synchronously on both ends to reduce fixed pattern noise and improve the imaging system modulation transfer function.

Figure 1:
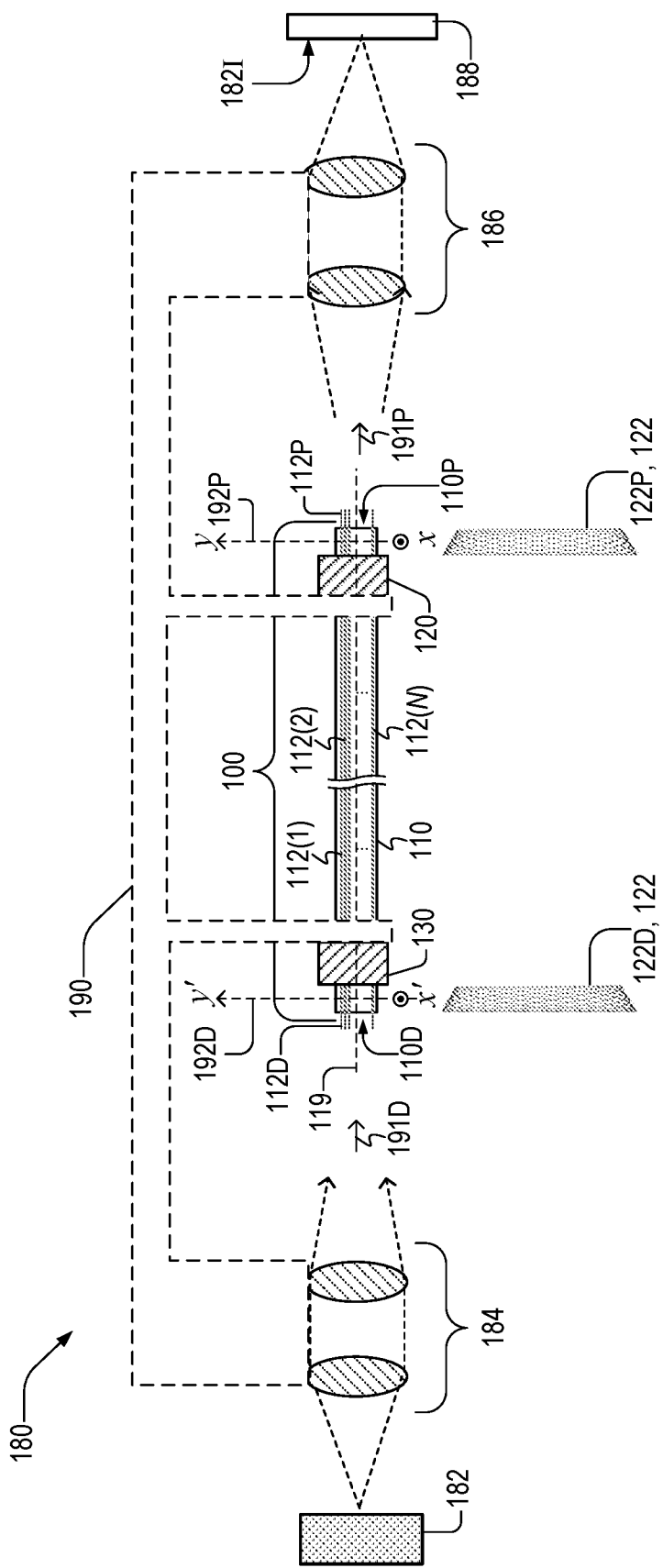
FIG. 1 is a schematic view of an embodiment of a dithered fiber-bundle imager in an embodiment of an imaging system where the fiber bundle is vibrated relative to lens and housing.

FIG. 1 shows one dithered fiber-bundle imager 100 as part of an imaging system 180. Imaging system 180 forms an image 182I of an object 182 on an image sensor 188 via a distal imaging objective 184, dithered fiber-bundle imager 100, and proximal imaging objective 186. Dithered fiber-bundle imager 100 includes a coherent fiber imaging bundle 110, a first piezoelectric actuator 120, and a second piezoelectric actuator 130. At least one of piezoelectric actuator 120, piezoelectric actuator 130, objective 184, and objective 186 may be mounted to be stable relative to a mount 190, which may be an endoscope tube. Mount 190 is a housing, for example. For sake of brevity, coherent fiber imaging bundle 110 is hereinafter referred to as fiber imaging bundle 110.

Figure 4B:
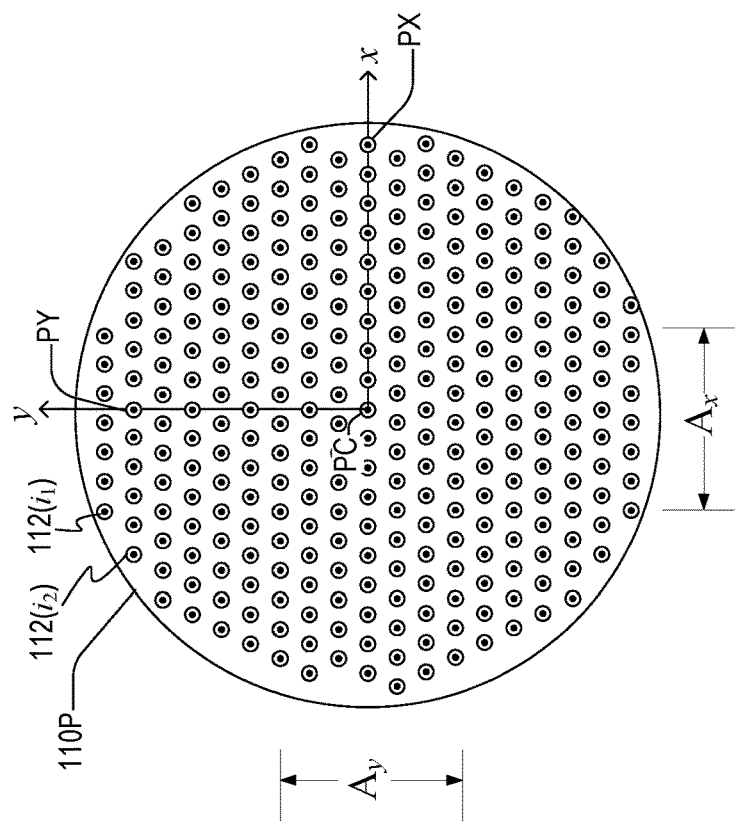
FIGS. 4A and 4B are respective plan views of a distal end and proximal end of a fiber imaging bundle of dithered fiber-bundle imager of FIG. 1, in an embodiment.
Figure 4A:
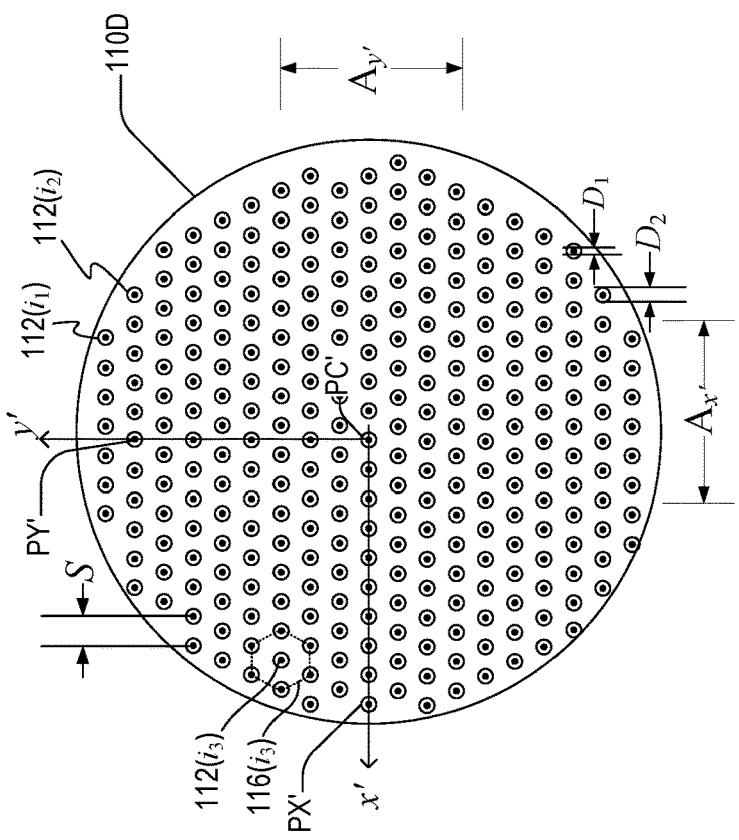

Fiber imaging bundle 110 includes a plurality of optical fibers 112(1, 2, ..., N), a proximal bundle end 110P, a distal bundle end 110D, and a central axis 119. Each optical fiber 112 has a respective axis. Central axis 119 may correspond to the optical axis of an optical fiber 112 at a geometric center of the fiber bundle formed by optical fibers 112. Quantity N is for example 30,000. FIGS. 4A and 4B are respective plan views of distal bundle end 110D and proximal bundle end 110P. FIGS. 1-3 are best viewed together in the following description.

Each optical fiber 112 has a fiber diameter $D_2$ and a core diameter $D_1$, a respective proximal end 112P exposed on proximal bundle end 110P, and a respective distal end 112D exposed on distal bundle end 110D. Fiber diameter $D_2$ is, for example, 0.75±0.10 mm. The optical axis of each optical fiber 112 is (a) parallel to a proximal longitudinal direction 191P at proximal bundle end 110P, and (b) parallel to a distal longitudinal direction 191D at distal bundle end 110D. For simplicity of illustration, directions 191P and 191D are shown as parallel to each other. As fiber imaging bundle 110 is flexible, e.g., sufficiently so for endoscopic applications, directions 191P and 191D are generally not parallel. FIG. 1 includes a distal plane 192D and a proximal plane 192P, which define orthogonal directions (x',y') and (x,y), respectively. Directions 191D and 191P are orthogonal to planes 192D and 192P, respectively. Herein, references to directions x, y, x', or y' are references to said directions as illustrated in FIG. 1, unless otherwise specified.

There are other ways to shift an image on fiber imaging bundle 110 than shifting the bundle. Dithering may be achieved by shifting a lens in the light path. A spherical lens vibrated in X and Y axes will shift or dither an image focused through that lens. Effectively, what matters is relative position of lens axis and the image it forms on the fiber bundle. In an alternative embodiment 380, as illustrated in FIG. 3, piezoelectric actuators 321, 331 are coupled to vibrate one or more components of the lens systems while the fiber bundle remains stationary relative to mount 190. For brevity, vibrating off-axis spherical lenses, vibrating off-axis cylindrical lenses, or vibrating other components of the lens system to shift or dither an image on a stationary fiber bundle end is referred to herein as vibrating the lens. Remaining components illustrated on FIG. 3 resemble those on FIG. 1, and their descriptions will not be repeated here for brevity.

It should be noted that, in both the embodiments of FIG. 1 and FIG. 3, the piezoelectric actuators vibrate the fiber bundle relative to the lens such that the image of object 182 is dithered across an end of the fiber bundle, but they differ in whether the lens or the bundle vibrates relative to a housing or mount.

FIG. 4A illustrates distal bundle end 110D with locations PC', PX' and PY' which, with central axis 119, define directions ±x' and ±y', and corresponding coordinate plane (x',y'), on distal bundle end 110D. Locations PC', PX' and PY' are, for example, locations of respective axes of two different optical fibers 112($m_0$), 112($m_1$) and 112($m_2$), where $m_{0,1,2} \in \{1, 2, \ldots, N\}$. FIG. 4B illustrates proximal bundle end 110P with locations PC, PX and PY which, with central axis 119, define directions ±x and ±y and corresponding coordinate plane (x,y) on proximal bundle end 110P. Locations PC, PX and PY are, for example, locations of respective axes of the same optical fibers 112($m_0$), 112($m_1$) and 112($m_2$) that define directions ±x' and ±y'. Coordinates (x,y) and (x',y') are in planes 192P and 192D, respectively.

Core centers of adjacent optical fibers 112 are separated by an inter-fiber spacing S. Each fiber 112 may be viewed as being at the center of a respective hexagonal region 116. For example, fiber 112($i_3$) is at the center of hexagonal region 116($i_3$), which has a maximum width 2S in the x direction (or x' direction, equivalently), and a maximum height √3S in the y direction (or y' direction, equivalently). Optical fibers 112 may be close-packed (e.g., in a hexagonal lattice) such that inter-fiber spacing S equals fiber diameter $D_2$.

First piezoelectric actuator 120 is configured to impart a trajectory 122P on proximal bundle end 110P in plane 192P that is orthogonal to direction 191P. Second piezoelectric actuator 130 is configured to impart trajectory 122D on distal bundle end 110D in plane 192D that is orthogonal to direction 191D.

First piezoelectric actuator 120 may be a tube actuator and may enclose proximal bundle end 110P. Second piezoelectric actuator 130 may be a tube actuator and may enclose distal bundle end 110D.

In an embodiment, trajectories 122D and 122P are equal such that bundle ends 110P and 110D move synchronously, which eliminates relative motion therebetween that would blur image 182I. Hereinafter, embodiments of dithered fiber-bundle imager 100 have trajectories 122D and 122P being equal to a common trajectory 122. Time dependence of common trajectory 122 may be expressed as $x(t)=x'(t)=A_x \cos(f_x t)$ and $y(t)=y'(t)=A_y \cos(f_y t+\delta)$, and may follow a Lissajous curve. In an embodiment, amplitudes $A_x$ and $A_y$ are determined such that common trajectory 122 uniformly covers hexagonal region 116 associated with a fiber 112. Such uniform coverage may be both spatially uniform and temporally uniform, e.g., within a time interval corresponding to a period of the Lissajous curve. For example, amplitude $A_x \geq S$ and amplitude $A_y \geq \sqrt{3}S/2$. Common trajectory 122 may be a trajectory other than the above-mentioned x(t) and y(t), e.g., any trajectory, without departing from the scope hereof.

Piezoelectric actuators 120 and 130 are configured to impart movement on respective bundle ends 110P and 110D, per x(t) and y(t) for example. The movement is, for example, (i) periodic motion in the x direction having a frequency $f_x$ and (ii) periodic motion in the y direction having a frequency $f_y$. Frequencies $f_x$ and $f_y$ may be chosen such that trajectories 122P, 122D uniformly sample respective planes 192P, 192D. Applicant has found that setting $|f_x - f_y| > 50$ Hz results in adequately uniform sampling for typical frame rates.

In an embodiment, piezoelectric actuators 120 and 130 are piezoelectric tubes (outer diameter 3.2±0.2 mm, I.D. 2.2±0.2 mm, length of 30 mm) that are configured to produce deflections in respective planes 192P and 192D. The deflection amplitude is, for example, between five micrometers and one hundred micrometers. Deflection is linearly proportional to voltage. The piezoelectric actuators 120 and 130 are driven by electrical amplifiers designed for piezoelectric actuators. The amplifiers in turn are driven by two signal generators, one for each orthogonal axis, e.g., (x,y) or (x',y').

Because of the methods used for developing the system (for example, mounting of the piezoelectric actuators 120, 130 in the system, and the fixation of the optical fiber to the piezoelectric actuators 120, 130), equivalent voltages on both the distal and proximal ends of the optical fiber may, in an embodiment, not produce equivalent deflections in the transverse plane. This is due to a non-equivalent length of piezoelectric tube protruding from the mount, as well as non-equivalent lengths of fiber protruding from the end of the piezoelectric tube. There is also a possible effect on the system due to tolerances in capacitance on the piezoelectric tube (e.g., 2.1 nF, with a tolerance of ±20%). The result of all of these effects is a difference in the transverse deflections by each piezoelectric tube along the various axes. In this embodiment, this could be corrected by the use of a voltage-dividing circuit, with one component being a potentiometer. Through this, the voltage going to either side is variable, which allows for the correction of the voltage while both piezoelectric tubes are running. The resultant voltages were determined by visual inspection of the images as voltages were varied, and the voltages were chosen to provide the best image quality.

Figure 5:
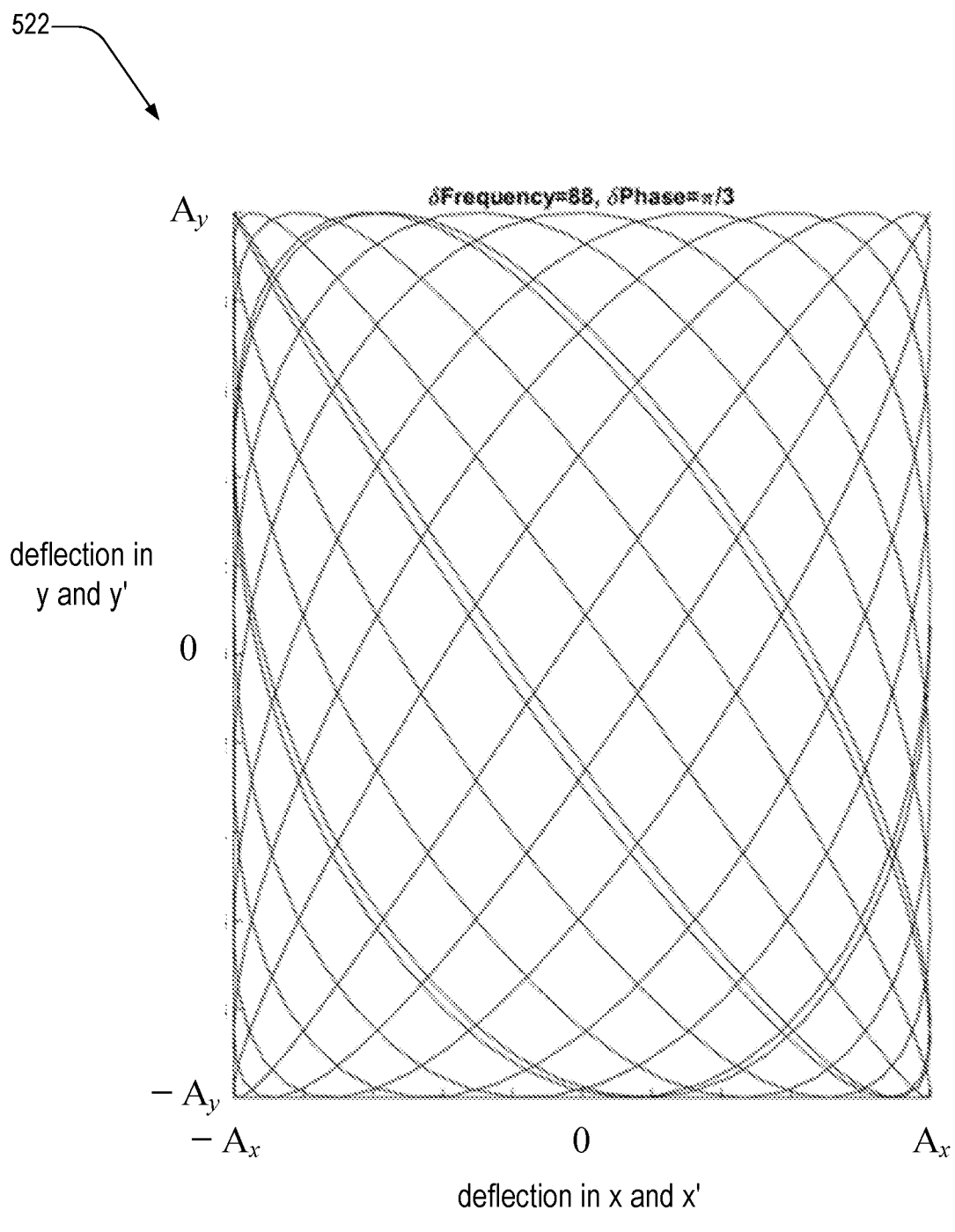
FIG. 5 depicts an exemplary trajectory of the distal end and proximal end of the dithered fiber-bundle imager of FIG. 1, in an embodiment.

In an embodiment, $|f_x-f_y|=88$ Hz and $\min(f_x, f_y)=500$ Hz, which corresponds to ten periods of motion during a twenty-millisecond exposure time. FIG. 5 illustrates a trajectory 522 corresponding to these parameters. Trajectory 522 is an example of common trajectory 122. In other embodiments, the frequency is chosen to provide a multiple greater than four of periods of motion of the lowest frequency actuator during each exposure time, and the difference in frequency between frequencies $f_x$ and $f_y$ being at least 50 Hz.

Figure 6:
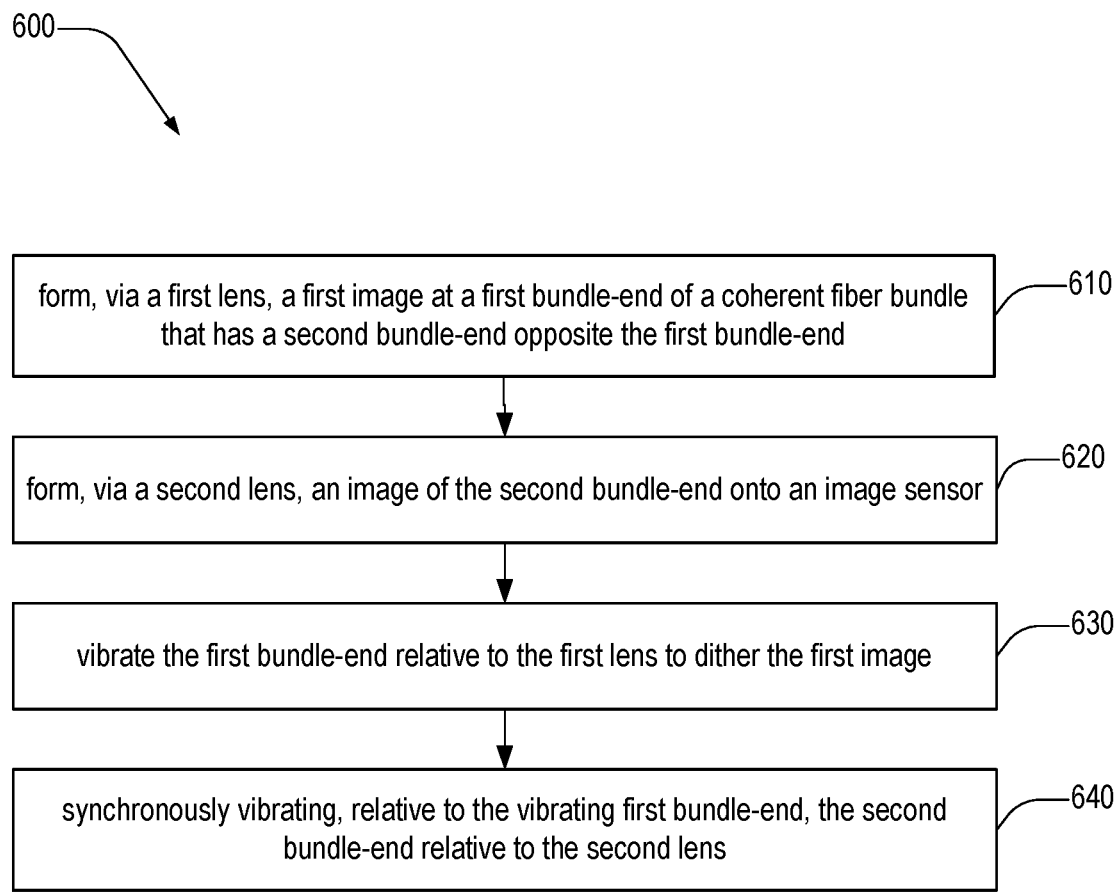
FIG. 6 is a flowchart of a method of high-resolution imaging using an embodiment of a dithered fiber-bundle imager, in an embodiment.

FIG. 6 is a flowchart illustrating a method 600 for high-resolution imaging. Method 600 includes at least one of steps 610, 620, 630, and 640. Step 610 is one of forming, using a first lens, a first image at a first bundle-end of a fiber imaging bundle that has a second bundle-end opposite the first bundle-end. In an example of step 610, objective 184 forms an image of object 182 on distal bundle end 110D, as shown in FIG. 1.

Step 620 is one of forming, using a second lens, an image of the second bundle-end onto an image sensor. In an example of step 620, objective 186 forms an image 182I of proximal bundle end on image sensor 188. Step 630 is one of vibrating the first bundle-end relative to the first lens to dither the first image. In an example of step 630, piezoelectric actuator 130 vibrates distal bundle end 110D relative to objective 184. In a second example of step 630, piezoelectric actuator 331 vibrates objective 184 relative to distal bundle end 110D.

Step 640 is one of synchronously vibrating, relative to the vibrating first bundle-end, the second bundle-end relative to the second lens. In an example of step 640, piezoelectric actuator 130, synchronously vibrates, relative to vibrating distal bundle end 110D, proximal bundle end 110P relative to objective 186. In a second example of step 640, piezoelectric actuator 321 vibrates objective 186 relative to proximal bundle end 110P.

Resultant Images

Figure 7:
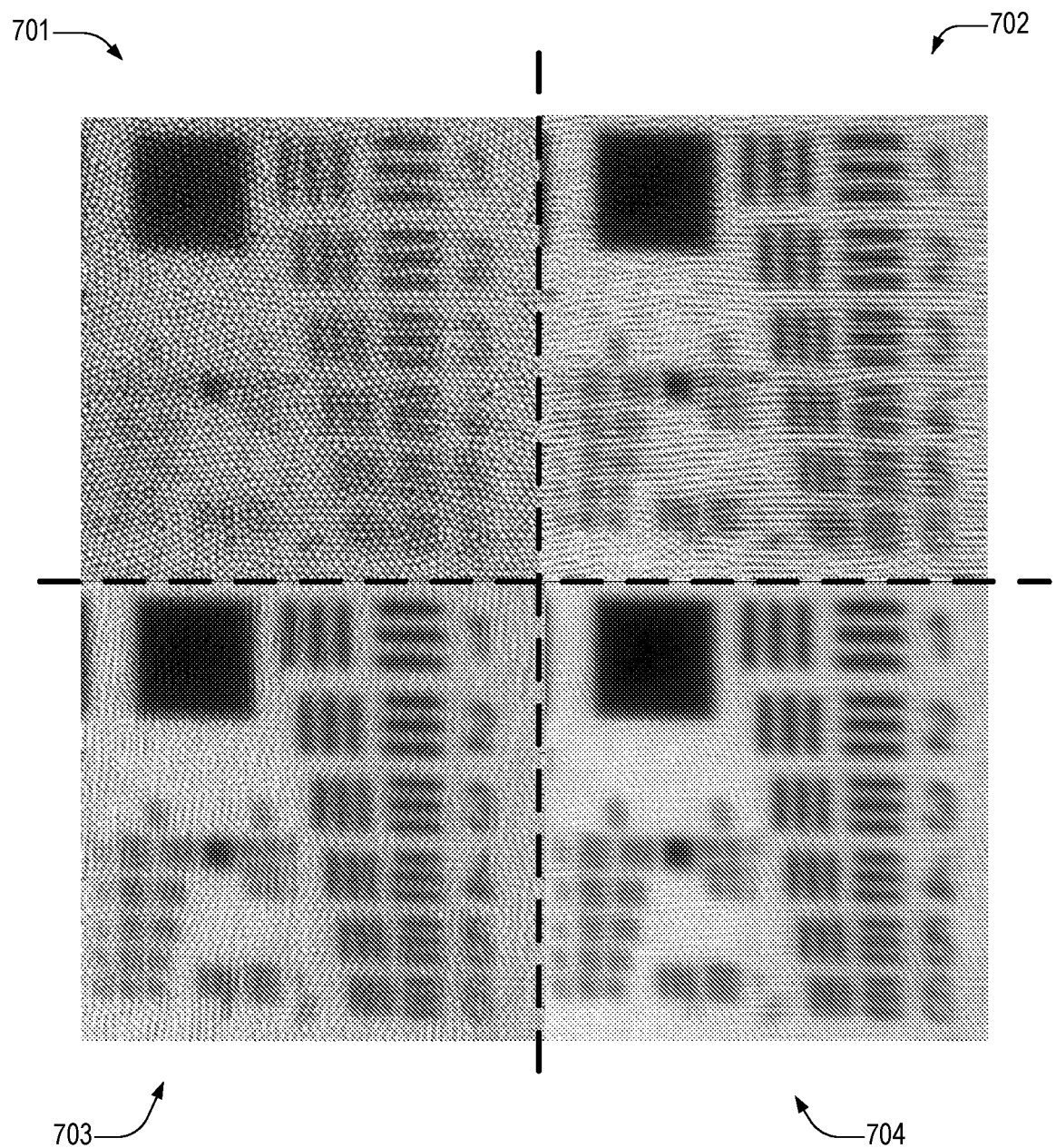
FIG. 7 includes are images of a test pattern obtained using an embodiment without dithering, with dithering in single axes, and with dithering in both axes.

Applicant evaluated the efficacy of method 600 using images obtained from a 1951 United States Air Force resolution test chart, shown in images 701, 702, 703, and 704 of FIG. 7. Image 701 is an image obtained with no dithering. Images 702 and 703 show image results with dithering in the x direction and in the y direction, respectively. Image 704 shows the result with dithering motion in both the ±x and ±y directions, using sinusoidal oscillations frequencies of 500 Hz and 588 Hz, respectively.

It is apparent from images 701-704 that dithering reduces fixed pattern noise due to the fiber structure. It is also apparent that motion in both directions is required to achieve the best performance. While the fixed pattern noise is reduced with dynamic dithering, it is not entirely eliminated. Comparison of images 701 and 704 illustrates that dithering improves the spatial resolution. The 242 line pairs per millimeter (lp/mm) spatial frequency for the resolution limit without dithering roughly corresponds to the frequency of the group 7, element 6 bars (228 lp/mm), located in the bottom right in the figure. Evaluation of image 701 shows that the resolution may be slightly worse, but it is close to that frequency. In image 704 it could be argued that the bar target is resolved out to group 8, element 2, (287 lp/mm), which is an improvement but not nearly as good as the theoretical limit of 814 lp/mm of this particular fiber bundle due to the size of core diameter $D_1$ of optical fiber 112. If that theoretical spatial resolution was achieved, the bars of group 9 element 5 would be resolved.

Figure 8:
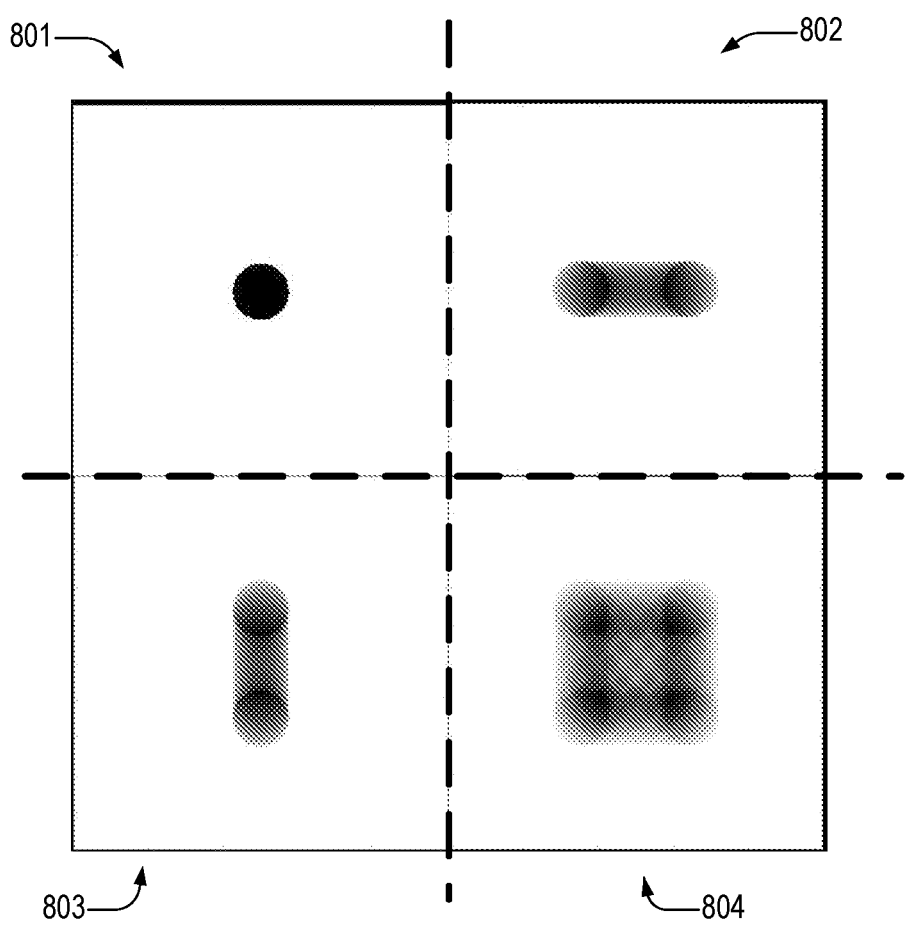
FIG. 8 includes images of a single fiber simulated without dithering, with dithering in single axes, and with dithering in both axes.

The experimental results show that the fixed pattern noise of fiber bundle imaging is greatly reduced but not entirely eliminated by the synchronous dithering. Moreover, the spatial resolution is also improved by dithering but not by as much as theoretically predicted. One possible reason for failure to reach resolution equivalent to the core size of the fibers is the scan pattern of the dithering motion. FIG. 8 shows calculated images 801, 802, 803, and 804 of the scan patterns of a single fiber core under the conditions of dithering motion used to obtain the images 701-704.

Without dithering, there is no motion and the single circular fiber core is stationary, as shown in image 801. With a sinusoidal signal in the x direction, there is a sinusoidal motion of the core in the x direction and the fiber distribution is spread out along that direction (image 802). With sinusoidal motion, the fiber slows down and reverses direction at the ends of the scan and therefore the fiber core spends more time at the motion extremes than at the center. The intensity of the pattern indicates how much time is spent integrating signal from the object over the two-dimensional plane of the object. The same pattern is observed in the y direction in image 803 when the sinusoidal signal is applied to the actuator's y channel. When a 500-Hz sinusoidal signal is applied in the x direction and a 588 Hz sinusoidal signal is applied in the y direction the pattern is spread out over the x, y plane image 804. While the hexagonal area of a single core cell is covered, the intensity, which effectively represents sampling sensitivity, is not uniform. This effect may be overcome by using non-sinusoidal waveforms, such as triangular waveforms, in the signal generators and amplifiers that drive the piezoelectric actuators (e.g., actuators 120, 130, 321, 331) to vibrate the fiber bundle or lens.

If a sinusoidal deflector waveform is applied to the actuator's x channel, and a ninety-degree phase-shifted version of that waveform is applied to the actuator's y channel, the resulting Lissajous pattern is a circle. If the sinusoidal deflector waveform is amplitude-modulated with a triangular modulation waveform of increasing amplitude from zero to a maximum deflector voltage throughout a modulation cycle, the resulting Lissajous pattern is a uniformly-spaced spiral.

Since motion of light deflection along a uniformly-spaced spiral is slower near the center than at the periphery, an integral seen by a camera of light from a fiber core deflected according to a uniformly-spaced spiral is denser towards the center of the pattern than the periphery. If the modulation waveform increases along an arc from zero to the maximum deflector voltage along a curve having a positive but monotonically decreasing first derivative in each cycle, the resulting spiral is more widely spaced near the center of the deflection pattern than near the periphery.

Figure 9A:
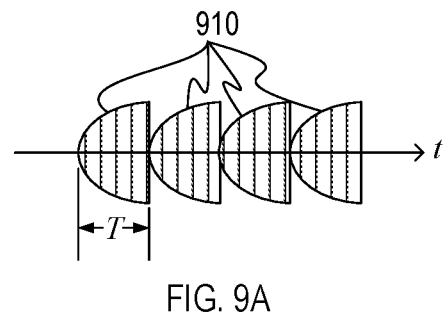
FIGS. 9A and 9B illustrate amplitude modulated waveforms for generating a spiral trajectory more widely spaced near a center of the spiral than near a periphery of the spiral.

For example, common trajectory 122 may be expressed by x(t) and y(t), where $x(t)=A_0 t^\alpha \sin(ft)$ and $y(t)=A_0 t^\alpha \cos(ft)$, where amplitude $A_0$ is a constant, and exponent $\alpha<1$, e.g., $\alpha=\frac{1}{2}$. Time t ranges from $t_m$ to $t_m+T$, where trajectory period $T=0.5\ f^{-1}$ and m is an integer indexing times t when x(t)=0. Frequency f is, for example, between 400 Hz and 1.0 kHz. FIG. 9A illustrates an envelope function 910 representing repeated instances of x(t) over a period T without the sinusoidal time dependence. To ensure consistent sampling within a sequence captured images, trajectory period T may be determined such that an integer multiple of trajectory period T equals at least one of an image-capture frame rate and an exposure time associated with image sensor 188, FIG. 1. The integer multiple is, for example, between five and twenty. Such a relationship between trajectory period and image-capture frame rate and/or an exposure time may apply to any trajectory 122 disclosed herein, there trajectory 122 periodically repeats.

Figure 10:
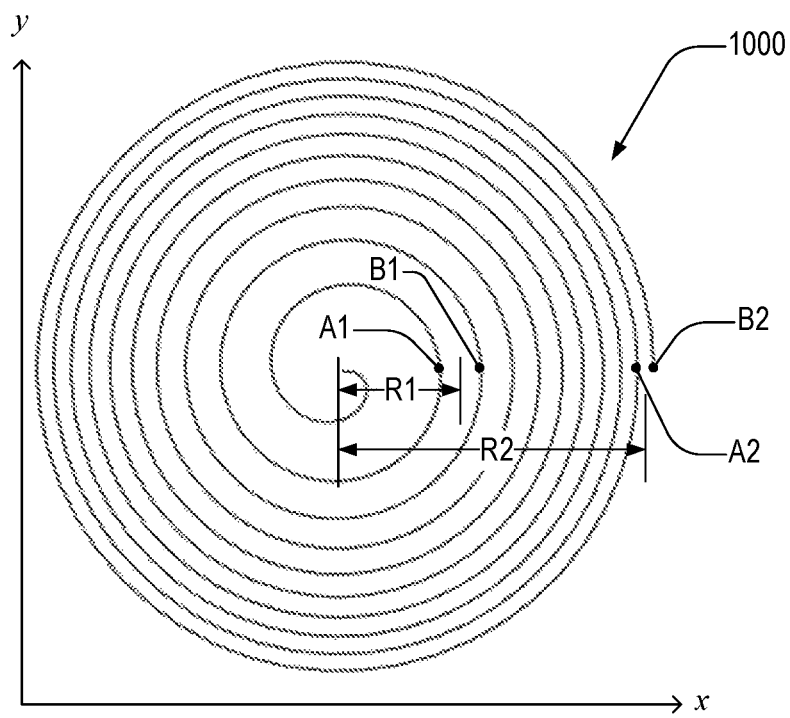
FIG. 10 illustrates a spiral trajectory useful in an embodiment for dithering.

FIG. 10 illustrates such as spiral 1000, traced from its center to its periphery. An integral seen by a camera of light from a fiber core deflected according to a spiral more widely spaced in center than in periphery is more nearly uniform across the deflection pattern than an integral seen by a camera of light from the fiber core deflected according to a uniformly-spaced spiral.

Figure 9B:
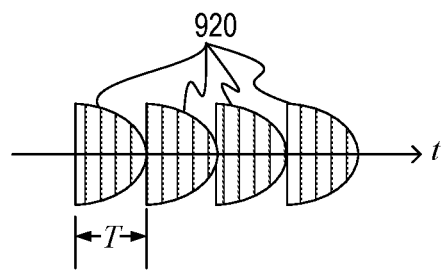

Modulation waveform of FIG. 9A may be time-reversed as illustrated in FIG. 9B, illustrating envelope function 920, to trace the spiral from periphery of the deflection pattern to center. Here, the traced amplitude modulation waveform monotonically decreases and has a negative and monotonically decreasing first derivative in each modulation cycle.

In alternative embodiments, piezoelectric actuators 120, 130, or 221, 231 are driven in x and y axes by amplitude-modulated, same-frequency waveforms having ninety-degree phase shift between the x and y axes with the amplitude modulation increasing along an arc from zero to a maximum deflector voltage along a curve having a positive but monotonically decreasing first derivative in each cycle, as illustrated in FIG. 9A such that the image focused on bundle end shifts relative to the fiber bundle end in a spiral pattern more widely spaced near the center of the deflection pattern as illustrated in FIG. 10 than near the periphery of the spiral, the spiral being traced from center to periphery.

In additional alternative embodiments, piezoelectric actuators 120, 130, or 221, 231 are driven in x and y axes by amplitude-modulated, same-frequency waveforms having ninety-degree phase shift between the x and y axes with the amplitude modulation decreasing along an arc from a maximum to a minimum deflector voltage along a curve having a negative and monotonically decreasing first derivative in each cycle, as illustrated in FIG. 9B such that the image focused on bundle end shifts relative to the fiber bundle end in a spiral pattern more widely spaced near the center of the deflection pattern as illustrated in FIG. 10 than near the periphery of the spiral, the spiral being traced from periphery to center. In particular embodiments, the spiral pattern provides uniform coverage of a unit cell covered by relative motion of a single fiber of the fiber bundle.

In additional alternative embodiments, piezoelectric actuators 120, 130, or 221, 231 are driven in x and y axes by amplitude-modulated drive waveforms having ninety-degree phase shift between the x and y axes to produce an evenly-spaced spiral, where the angular frequency of the x and y axis drive waveforms that decrease as a function of increasing spiral radius. For example, spiral 1000 includes points A1, B1 near a first radius R1 and points A2 and B2 near a second radius R2> R1. When spiral 1000 has a radius-dependent angular frequency, the angular velocity of its trajectory points A1 and B1 exceeds that of the trajectory between points A2 and B2. For example, the angular velocity of the trajectory monotonically decreases between points A1 and B2. In this embodiment, the piezoelectric actuator is configured so a small-radius turn of the spiral (e.g., at radius R1) is performed in less time than a large-radius turn of the spiral (e.g., at radius R2).

In an alternative embodiment, the tubular piezoelectric actuator is configured to vibrate a first end of the fiber bundle relative to an image stationary relative to a housing, while at a second end of the fiber bundle actuators are used to vibrate a lens element positioned to image the second end of the fiber bundle on an image sensor of a digital camera. The magnification and vibration of the lens element and fiber bundle are adjusted so relative motion of image and bundle match at each end of the bundle.

Combinations

The features herein described may be combined in various ways to make a usable imaging device, some but not all of which are given below:

A dithered fiber-bundle imager designated A1 includes a fiber imaging bundle including (i) a plurality of optical fibers, (ii) a proximal bundle end exposing a respective proximal end of each of the plurality of optical fibers, and (iii) a distal bundle end exposing a respective distal end of each of the optical fibers. Each of the optical fibers has a respective optical axis parallel to (a) a proximal longitudinal direction at the proximal bundle end, and (b) a distal longitudinal direction at the distal bundle end. The imager also includes a first piezoelectric actuator configured to move a proximal device in a proximal plane orthogonal to the proximal longitudinal direction. The proximal device is one of (i) the proximal bundle end and (ii) a proximal lens. The imager also include a second piezoelectric actuator configured to move a distal device in a distal plane orthogonal to the distal longitudinal direction, such that motion of the distal device and the proximal device are synchronized. The distal device is one of (i) the distal bundle end and (ii) a distal lens.

A dithered fiber-bundle imager designated A2 including the dithered fiber-bundle imager designated A1 where the distal device is the distal bundle end and the first piezoelectric actuator is a piezoelectric tube actuator enclosing the fiber imaging bundle near the proximal bundle end, and the proximal device is a proximal bundle end and the second piezoelectric actuator is a tube actuator enclosing the fiber imaging bundle near distal bundle end.

A dithered fiber-bundle imager designated A3 including the dithered fiber-bundle imager designated A1 where the first piezoelectric actuator is coupled to vibrate the proximal lens.

A dithered fiber-bundle imager designated A4 including the dithered fiber-bundle imager designated A1, A2, or A3, the proximal plane and the distal plane having orthogonal x and y directions, the first piezoelectric actuator imparting (i) periodic motion in the x direction having a frequency $f_x$ and (ii) periodic motion in the y direction having a frequency $f_y$, such that a difference between $f_x$ and $f_y$ exceeds 50 Hz such that the trajectory uniformly covers the proximal plane.

A dithered fiber-bundle imager designated A5 including the dithered fiber-bundle imager designated A4 wherein the periodic motions are non-sinusoidal.

A dithered fiber-bundle imager designated A6 including the dithered fiber-bundle imager designated A1, A2, A3, A4, or A5 wherein the imager is configured to focus an image from the proximal bundle end onto an electronic image sensor.

A dithered fiber-bundle imager designated A7 including the dithered fiber-bundle imager designated A1, A2, A3, A4, A5, or A6 the proximal and distal planes having orthogonal x and y directions, the plurality of optical fibers each having a fiber diameter, the trajectory having, in a plane parallel to the x-y plane, at least one of an x-direction amplitude and a y-direction amplitude being at least √3/2 times the fiber diameter.

A dithered fiber-bundle imager designated A8 including the dithered fiber-bundle imager designated A1, A2, A3, A4, A5, A6, or A7, the first piezoelectric actuator configured to move the proximal end in a Lissajous-curve trajectory, the second piezoelectric actuator configured to move the distal end in the Lissajous-curve trajectory.

A dithered fiber-bundle imager designated A9 including the dithered fiber-bundle imager designated A1, A2, or A3, the piezoelectric actuator configured to move the proximal device, in the proximal plane, in a spiral trajectory.

A dithered fiber-bundle imager designated A10 including the dithered fiber-bundle imager designated A1, A2, or A3, the spiral trajectory being more widely spaced near a center of the spiral than near a periphery of the spiral.

A dithered fiber bundle imager designated A11 including the dithered fiber bundle imager designated A9 or A10, the spiral trajectory having an angular velocity that decreases as a function of increasing distance of the proximal device from a center of the spiral trajectory.

A method for high-resolution imaging designated B1 includes: (i) forming, via a first lens, a first image at a first bundle-end of a fiber imaging bundle that has a second bundle-end opposite the first bundle-end and (ii) forming, via a second lens, an image of the second bundle-end onto an image sensor. The method also includes (iii) vibrating the first bundle-end relative to the first lens to dither the first image, and (iv) synchronously vibrating, relative to the vibrating first bundle-end, the second bundle-end relative to the second lens.

In a method of high-resolution imaging designated B2 including the method designated B1, the step of the vibrating of the first bundle-end includes vibrating the first bundle-end at a first frequency in a first axis perpendicular to an optical axis of the fiber imaging bundle and vibrating at a second frequency in a second axis perpendicular to both the optical axis and the first axis.

In a method of high-resolution imaging designated B3 including the method designated B1 or B2, at least one of: (a) the step of vibrating the first bundle-end being performed by a first piezoelectric actuator configured to vibrate the first bundle-end relative to a housing, and (b) the step of vibrating the second bundle-end being performed by a second piezoelectric actuator configured to vibrate the second bundle-end relative to the housing.

In a method of high-resolution imaging designated B4 including the method designated B1, B2, or B3, at least one of (a) the piezoelectric actuator being a piezoelectric tube disposed about the first bundle-end, and (b) the second piezoelectric actuator being a piezoelectric tube disposed about the second bundle-end.

In a method of high-resolution imaging designated B8 including the method designated B1, the vibrating of the first bundle-end relative to the lens describing a repeated spiral at a first frequency.

In a method of high-resolution imaging designated B9 including the method designated B8, wherein the vibrating of the first bundle-end describing a spiral follows a spiral more widely spaced near a center of the spiral than near a periphery of the spiral.

In a method of high-resolution imaging designated B6 including the method designated B2, B3, B4, or B5, the first frequency and the second frequency differ by at least fifty hertz.

In a method of high-resolution imaging designated B7 including the method designated B2, B3, B4, B5, or B6, the first frequency exceeding five hundred hertz.

In a method of high-resolution imaging designated B8 including the method designated B2, B3, B4, B5, B6, or B7, the fiber imaging bundle includes a plurality of optical fibers each having a respective one of a plurality of parallel optical axes, (a) the step of vibrating the first bundle-end includes vibrating the first bundle-end in two orthogonal directions each perpendicular to the plurality of parallel optical axes at the first bundle-end, and (b) the step of vibrating the second bundle-end includes vibrating the second bundle-end in two orthogonal directions each perpendicular to the plurality of parallel optical axes at the second bundle-end.

In a method of high-resolution imaging designated B9 including the method designated B2, B3, B4, B5, B6, B7, or B8, the step of synchronously vibrating the second bundle-end includes vibrating the second bundle-end such that the second bundle-end and the first bundle-end move in a same trajectory.

In a method of high-resolution imaging designated B10 including the method designated B8 or B9, the spiral trajectory having an angular velocity that decreases as a function of increasing distance, from a center of the spiral trajectory, of one of the of the proximal device and the first lens.

Changes may be made in the above methods and systems without departing from the scope hereof. It should thus be noted that the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall therebetween.

The invention claimed is:

1. A dithered fiber-bundle imager, comprising:
a fiber imaging bundle including (i) a plurality of optical fibers, (ii) a proximal bundle end exposing a respective proximal end of each of the plurality of optical fibers, and (iii) a distal bundle end exposing a respective distal end of each of the optical fibers, each of the optical fibers having a respective optical axis parallel to (a) a proximal longitudinal direction at the proximal bundle end, and (b) a distal longitudinal direction at the distal bundle end;
a first piezoelectric actuator configured to move a proximal device along a trajectory in a proximal plane orthogonal to the proximal longitudinal direction, the proximal device being one of (i) the proximal bundle end and (ii) a proximal lens; and
a second piezoelectric actuator configured to move a distal device in a distal plane orthogonal to the distal longitudinal direction, such that motion of the distal device and the proximal device are synchronized, the distal device being one of (i) the distal bundle end and (ii) a distal lens,
the proximal plane and the distal plane having orthogonal x and y directions,
the first piezoelectric actuator configured to impart (i) a first periodic motion in the x direction having a frequency $f_x$ and (ii) a second periodic motion in the y direction having a frequency $f_y$;
a difference between frequencies $f_x$ and $f_y$ exceeding 50 Hz such that the trajectory uniformly covers the proximal plane,
each of frequency $f_x$ and frequency $f_y$ exceeding 400 Hz.

2. The dithered fiber-bundle imager of claim 1,
the proximal device being the proximal bundle end and the first piezoelectric actuator being a first tube actuator enclosing the fiber imaging bundle near the proximal bundle end,
the distal device being the distal bundle end and the second piezoelectric actuator being a second tube actuator enclosing the fiber imaging bundle near the distal bundle end.

3. The dithered fiber-bundle imager of claim 1, the first piezoelectric actuator being configured to vibrate the proximal lens.

4. The dithered fiber-bundle imager of claim 1, the first piezoelectric actuator configured to move the proximal device, in the proximal plane, in a spiral trajectory.

5. The dithered fiber-bundle imager of claim 4, the spiral trajectory being more widely spaced near a center of the spiral trajectory than near a periphery of the spiral trajectory.

6. The dithered fiber-bundle imager of claim 4, the spiral trajectory having an angular velocity that decreases as a function of increasing distance of the proximal device from a center of the spiral trajectory.

7. The dithered fiber-bundle imager of claim 1, the first periodic motion and the second periodic motion each being non-sinusoidal.

8. The dithered fiber-bundle imager of claim 1, the proximal lens being configured to form an image of the proximal bundle end onto an image sensor.

9. The dithered fiber-bundle imager of claim 1, the proximal and distal planes having orthogonal x and y directions, the plurality of optical fibers each having a fiber diameter, the trajectory having, in a plane parallel to the x-y plane, at least one of an x-direction amplitude and a y-direction amplitude being at least $\sqrt{3}/2$ times the fiber diameter.

10. The dithered fiber-bundle imager of claim 1, the first piezoelectric actuator configured to move the proximal bundle end in a Lissajous-curve trajectory, the second piezoelectric actuator configured to move the distal bundle end in the Lissajous-curve trajectory.

11. The dithered fiber-bundle imager of claim 1, the distal bundle end being disposed within an endoscope.

12. The dithered fiber-bundle imager of claim 1, each of frequency $f_x$ and frequency $f_y$ not exceeding 1.0 kHz.

13. A method for high-resolution imaging comprising:
forming, via a first lens, a first image at a first bundle-end of a fiber imaging bundle that has a second bundle-end opposite the first bundle-end;
forming, via a second lens, an image of the second bundle-end onto an image sensor;
vibrating the first bundle-end relative to the first lens to dither the first image;
synchronously vibrating, relative to the vibrating first bundle-end, the second bundle-end relative to the second lens; and
vibrating the first bundle-end at a first frequency in a first axis perpendicular to an optical axis of the fiber imaging bundle and vibrating at a second frequency in a second axis perpendicular to both the optical axis and the first axis,
the first frequency and the second frequency differing by at least 50 Hz, each of the first frequency and the second frequency exceeding 400 HZ.

14. The method of claim 13, at least one of: (a) the step of vibrating the first bundle-end being performed by a first piezoelectric actuator configured to vibrate the first bundle-end relative to a housing, and (b) the step of vibrating the second bundle-end being performed by a second piezoelectric actuator configured to vibrate the second bundle-end relative to the housing.

15. The method of claim 14, at least one of (a) the first piezoelectric actuator being a first piezoelectric tube disposed about the first bundle-end, and (b) the second piezoelectric actuator being a second piezoelectric tube disposed about the second bundle-end.

16. The method of claim 13, the step of vibrating comprising moving the first bundle-end relative to the first lens in a spiral trajectory at a first frequency.

17. The method of claim 16, the spiral trajectory being more widely spaced near a center of the spiral trajectory than near a periphery of the spiral trajectory.

18. The method of claim 13, each of frequency $f_x$ and frequency $f_y$ not exceeding 1.0 kHz.

* * * * *